(12) United States Patent
Wallingford et al.

(10) Patent No.: US 7,824,919 B2
(45) Date of Patent: Nov. 2, 2010

(54) METHOD FOR ANALYZING ACTIVATED POLYETHYLENE GLYCOL COMPOUNDS

(75) Inventors: Ross A. Wallingford, Scott Depot, WV (US); Maciej Turowski, Midland, MI (US)

(73) Assignees: Dr. Reddy's Laboratories Limited, Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 1584 days.

(21) Appl. No.: 11/072,763

(22) Filed: Mar. 4, 2005

(65) Prior Publication Data

US 2006/0198818 A1  Sep. 7, 2006

(51) Int. Cl.
*G01N 33/00* (2006.01)
(52) U.S. Cl. ...................... 436/128; 436/180
(58) Field of Classification Search ............ 436/180, 436/128
See application file for complete search history.

(56) References Cited

U.S. PATENT DOCUMENTS

| 5,366,735 | A | 11/1994 | Henry |
| 6,280,745 | B1 | 8/2001 | Flore et al. |
| 6,455,639 | B1 | 9/2002 | Yasukohchi et al. |
| 2005/0054816 | A1 | 3/2005 | McManus et al. |

OTHER PUBLICATIONS

Muir "Determination of poly(ethylene glycol) 300 in long chain free fatty acid mixtures by reversed phased high performance liquid chromatography" 1998, Journal of Chromatography A, vol. 810, issues 1-2, Jun. 12, 1998, pp. 241-244.*
Bioconjugate Chem., 1995, 6, p150-165.
Henmanson, Bioconjugate Techniques (1996) Chapter 15.
Roberts et al., Advanced Drug Delivery Reviews 54 (2002) p. 459-4.
Gorbunov et al., J. Chrom A, 955 (2002) 9-17.

(Continued)

*Primary Examiner*—Sam P Siefke
(74) *Attorney, Agent, or Firm*—Balaram Gupta; Thomas C. McKenzie; Robert A. Franks

(57) ABSTRACT

A chemical analysis method for the determination of $RO(CH_2CH_2O)_nH$, $RO(C_2H_4O)_nA$, and $AO(C_2H_4O)_nA$ in a mixture thereof, wherein R is an alkyl group, A is a functional group for coupling with a surface or a biologically active material or another thing of use and n is an integer greater than 10. The method includes the step of chromatographing a sample of the mixture by liquid chromatography under critical conditions to determine the relative amounts of $RO(CH_2CH_2O)_n H$, $RO(C_2H_4O)_nA$, and $AO(C_2H_4O)_nA$ in the mixture. In addition a chemical analysis method for the determination of $RO(CH_2CH_2O)_nH$, $RO(C_2H_4O)_nA$, and $AO(C_2H_4O)_nA$ in a mixture thereof, wherein R is an alkyl group, A is a functional group for coupling with a biologically active material and n is an integer greater than 10. The method includes two steps. The first step is derivatizing the A groups of the mixture with a derivatizing agent to form a derivatized mixture comprising $RO(CH_2CH_2O)_nH$, $RO(C_2H_4O)_nAD$, and $DAO(C_2H_4O)_nAD$, wherein AD is the derivatized A group. The second step is chromatographing a sample of the derivatized mixture by liquid chromatography under critical conditions to determine the relative amounts of $RO(CH_2CH_2O)_nH$, $RO(C_2H_4O)_nAD$, and $DAO(C_2H_4O)_nAD$ in the derivatized mixture.

12 Claims, 2 Drawing Sheets

OTHER PUBLICATIONS

Baran et al., J. Chrom. B, 753 (2001) 139-149.
Kazanskii et al., Polymer Science, Series A, vol. 42, No. 6 (2000), p. 585-595.
Rissler, J. Chrom. A, 742 (1996) 457.
Liu, et al., J. Chrom. A 1046 (2004) 121.
A. V. Gorshkov et al., "Chromatographic investigations of macromoleculkes in the "critical range" of liquid chromatography. I. Functionality type and composition distribution in polyethylene oxide and polypropylene oxide copolymers," Journal of Chromatography, vol. 523, pp. 91-102, 1990.
B. Trathnigg et al., "Analysis of polyethers by isocratic HPLC with universal detectors. I. Optimization of chromatographic conditions," Journal of Liquid Chromatography, vol. 16(12), pp. 2439-2452, 1993.
H. Pasch et al., "Chromatographic investigations of macromolecules in the critical range of liquid chromatography. VIII. Analysis of polyethylene oxides," Journal of Liquid Chromatography, vol. 17(14 &15), pp. 3091-3108, 1994.
B. Trathnigg et al., "Analysis of polyethers by isocratic HPLC with universal detectors. III. A study on reproducibility," Journal of Liquid Chromatography, vol. 17(19), pp. 4285-4302, 1994.
H. Pasch et al., "Use of matrix-assisted laser desorption/ionization mass spectrometry for molar mass-sensitive detection in liquid chromatography of polymers," Journal of Chromatography A, vol. 699, pp. 21-29, 1995.
S. Zalipsky, "Chemistry of polyethylene glycol conjugates with biologically active molecules," Advanced Drug Delivery Reviews, vol. 16, pp. 157-182, 1995.
G. Lapienis et al., "Preparation of monomethyl ethers of poly(ethylene glycol)s free of the poly(ethylene glycol)," Journal of Bioactive and Compatible Polymers, vol. 16, pp. 206-220, 2001.
T. Macko et al., "Liquid chromatography of synthetic polymers under critical conditions. The case of single eluents and the role of theta conditions," Macromolecules, vol. 35, pp. 1797-1804, 2002.
A. M. Skvortsov, "End-functionalized polymer as a tool to determine the pore size and the interaction parameters in liquid chromatography," Macromolecules, vol. 35, pp. 8609-8620, 2002.
C. Rappel et al., "Liquid chromatography of polyethylene glycol mono- and diesters: functional macromolecules or block copolymers?", Journal of Chromatography A, vol. 984, pp. 29-43, 2003.
I. Park et al., "Effect of block copolymer chain architecture on chromatographic retention," Macromolecules, vol. 36, pp. 8539-8543, 2003.
B. Trathnigg et al., "Characterization of ethoxylated fatty alcohols using liquid chromatography with density and refractive index detection. II. Quantification in liquid chromatography under critical conditions," Journal of Chromatography A, vol. 665, pp. 47-53, 1994.

* cited by examiner

METHOD FOR ANALYZING ACTIVATED POLYETHYLENE GLYCOL COMPOUNDS

BACKGROUND OF THE INVENTION

The instant invention relates to chemical analysis methods for analyzing polyethylene glycol compounds. More particularly, the instant invention relates to the analysis of polyethylene glycol compounds by liquid chromatography under "critical conditions". The polyethylene glycol compounds of the instant invention have been "activated" to facilitate chemical modification of physiologically active materials, which modified materials are applicable, for example, in drug delivery systems.

Biologically active compounds conjugated with polyoxyalkylenes can provide enhanced biocompatibility for the compound, See, for example, U.S. Pat. No. 5,366,735 and U.S. Pat. No. 6,280,745. A review of this subject by Zalipsky, in Bioconjugate Chem., 1995, 6, p 150-165, identified polyethylene glycol as one of the best biocompatible polymers to conjugate with a biologically active compound (such as a drug, a protein, a peptide or an enzyme) to produce a conjugate having improved properties such as compatible solubility characteristics, reduced toxicity, improved surface compatibility, increased circulation time and reduced immunogenicity.

Polyethylene glycol (PEG) is a linear polyoxyalkylene terminated at the ends thereof with hydroxyl groups and generally represented by the formula: $HO(CH_2CH_2O)_nH$. Monomethoxy polyethylene glycol (mPEG) is generally represented by the formula: $CH_3O(CH_2CH_2O)_nH$. mPEG can be "activated" with a group "A" that will couple with a group of the biologically active material. Activated mPEG is generally represented by the formula: $CH_3O(CH_2CH_2O)_nA$. For example, trichloro-s-triazine activated mPEG will couple to an amine group of a biologically active material, as discussed by Henmanson in Chapter 15 of Bioconjugate Techniques (1996).

More recently, so called "second generation" PEGylation chemistry has been developed to, for example, minimize problems of diol impurity contamination of mPEG, to increase the molecular weight of the mPEG and to increase stability of the conjugate, see Roberts et al., Advanced Drug Delivery Reviews 54 (2002) p 459-4. U.S. Pat. No. 6,455,639 described an increased molecular weight mPEG having narrow molecular weight distribution.

Liquid chromatography under critical conditions has become an important method for polymer analysis, see, for example, Gorbunov et al., J. Chrom A, 955 (2002) 9-17. Liquid chromatography under critical conditions has been used to determine polyethylene glycol in mPEG (see, for example, Baran et al., J. Chrom. B, 753 (2001) 139-149; and Kazanskii et al., Polymer Science, Series A, Vol 42, No. 6 (2000), p 585-595. However, the degree of resolution of the polyethylene glycol and mPEG peaks is poor when the molecular weight of the mPEG is 5,000 grams per mole or more (see FIG. 2 of the Kazanskii et al. reference). And, liquid chromatography under critical conditions has not been used to analyze activated mPEG.

SUMMARY OF THE INVENTION

The instant invention is the discovery that liquid chromatography under critical conditions can be used to analyze activated mPEG for residual mPEG alcohol, activated mPEG and activated PEG diol even when the molecular weight of the mPEG is 5,000 grams per mole or more. Furthermore, derivatization of the activated mPEG and activated diol according to the instant invention can increase their chromatographic resolution. In addition, derivatization of the activated mPEG and activated diol according to the instant invention can facilitate chromatographic detectability.

More specifically, the instant invention in one embodiment is a chemical analysis method for the determination of $RO(CH_2CH_2O)_nH$, $RO(C_2H_4O)_nA$, and $AO(C_2H_4O)_nA$ in a mixture thereof, wherein R is an alkyl group, A is a functional group for coupling with a surface or a biologically active material or an other thing of use and n is an integer greater than 10, comprising the step of: chromatographing a sample of the mixture by liquid chromatography under critical conditions to determine the relative amounts of $RO(CH_2CH_2O)_nH$, $RO(C_2H_4O)_nA$, and $AO(C_2H_4O)_nA$ in the mixture.

In another embodiment the instant invention is a chemical analysis method for the determination of $RO(CH_2CH_2O)_nH$, $RO(C_2H_4O)_nA$, and $AO(C_2H_4O)_nA$ in a mixture thereof, wherein R is an alkyl group, A is a functional group for coupling with a surface or a biologically active material or another thing of use and n is an integer greater than 10, comprising the steps of: (a) derivatizing the A groups of the mixture with a derivatizing agent to form a derivatized mixture comprising $RO(CH_2CH_2O)_nH$, $RO(C_2H_4O)_nAD$, and $DAO(C_2H_4O)_nAD$, wherein AD is the derivatized A group; and (b) chromatographing a sample of the derivatized mixture by liquid chromatography under critical conditions to determine the relative amounts of $RO(CH_2CH_2O)_nH$, $RO(C_2H_4O)_n AD$, and $DAO(C_2H_4O)_nAD$ in the derivatized mixture.

DETAILED DESCRIPTION

The compounds to be analyzed by one method of the instant invention are represented by the formulas I, II and III:

$$RO(C_2H_4O)_nA; \qquad (I)$$

$$AO(C_2H_4O)_nA; \text{and} \qquad (II)$$

$$RO(C_2H_4O)_nH \qquad (III)$$

wherein R represents a $C_{1-7}$ hydrocarbon group (usually a methyl group), n represents the average number of moles of $C_2H_4O$ groups, e.g., from 10 to 2000 and A is the "activating" group. In many applications, the compound of formula I is the desired material. The compound of formula III is non-activated PEG which is unreactive. The compound of formula II is deactivated PEG which is produced from PEG diol impurity. Thus, the sample to be analyzed usually consists primarily of the compound of formula I with relatively lower levels of the compounds of formulas II and III in a mixture. The relative amounts of the compounds of formula I, II and III are determined by chromatographing a sample of the mixture by liquid chromatography under critical conditions to determine the relative amounts of $RO(CH_2CH_2O)_nH$, $RO(C_2H_4O)_nA$, and $AO(C_2H_4O)_nA$ in the mixture. It should be understood that the instant invention in its full scope includes PEG copolymers (for example, random or block copolymers comprising $C_2H_4O$ groups) and any polymer topology such as linear, branched, comb and star topologies.

It should be understood that a certain degree of experimentation is required to achieve liquid chromatography under critical conditions. However, reference to the literature will direct the person of ordinary skill in the art of liquid chromatography to the necessary conditions, see, for example, Gorbunov et al., J. Chrim A, 955 (2002) 9-17. Critical condition LC tends to separate polymers based on the composition of the end groups of the polymer and is (in theory) independent of the polymers molecular weight. For example, if a reverse phase column is operated under critical conditions, then polymers with hydrophobic end groups can be separated from polymers with hydrophilic end groups.

EXAMPLE 1

Figure 1:
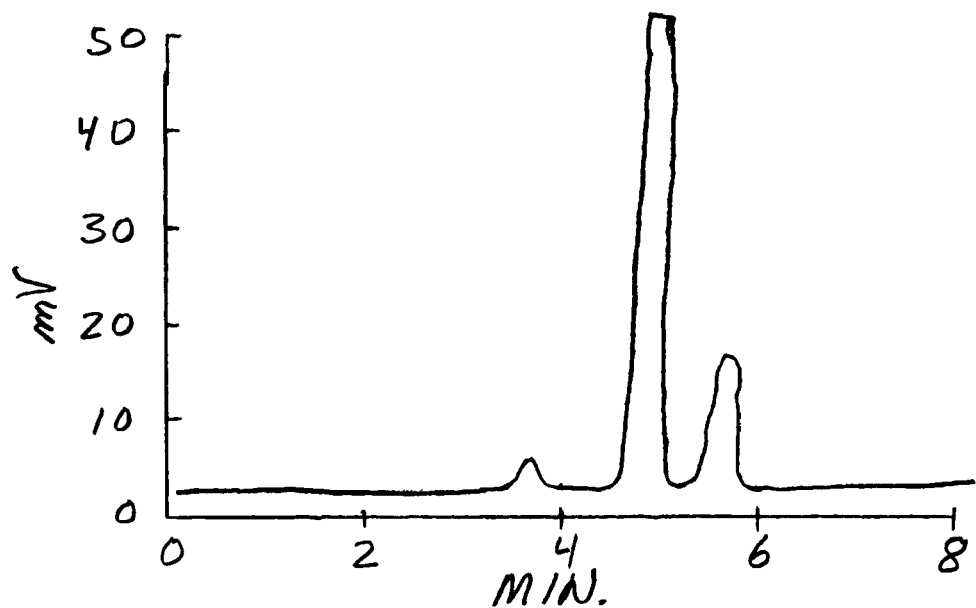
FIG. 1 is a reproduction of a chromatogram showing the separation of mPEG, propionaldehyde diacetal activated mPEG and propionaldehyde diacetal activated diol.

0.1 gram of propionaldehyde diacetal activated 5,000 weight average molecular weight mPEG is mixed with 3 milliliters of water to produce a sample for injection. 5 microliters of the sample for injection is injected into a mobile phase of 52% A and 48% B (where A is 47% acetonitrile in water and B is 43% acetonitrile in water) at a mobile phase flow rate of 0.75 milliliters per minute and flowed through a 5 micrometer packing diameter Supelco LC-18 reverse phase column at a column temperature of 30 degrees Celsius, the column having an internal diameter of 4.6 millimeters and a length of 250 millimeters, followed by an evaporative light scattering detector to produce the chromatogram shown in FIG. 1. The chromatogram of FIG. 1 shows a peak at about 3.8 minutes for mPEG, a peak at about 4.8 minutes for the activated mPEG and a peak at about 5.6 minutes for the activated diol. The mole percent concentration of mPEG is determined by dividing the peak area of the mPEG peak by the combined peak areas of the mPEG, the activated mPEG and the activated diol peak areas and then multiplying by 100. The mole percent concentration of activated mPEG is determined by dividing the peak area of the activated mPEG peak by the combined peak areas of the mPEG, the activated mPEG and the activated diol peak areas and then multiplying by 100. The mole percent concentration of activated diol is determined by dividing the peak area of the activated diol peak by the combined peak areas of the mPEG, the activated mPEG and the activated diol peak areas and then multiplying by 100.

Evaporative light scattering detection is well-known in liquid chromatography, see, for example, Rissler, J. Chrom. A, 742 (1996) 45.

EXAMPLE 2

Figure 2:
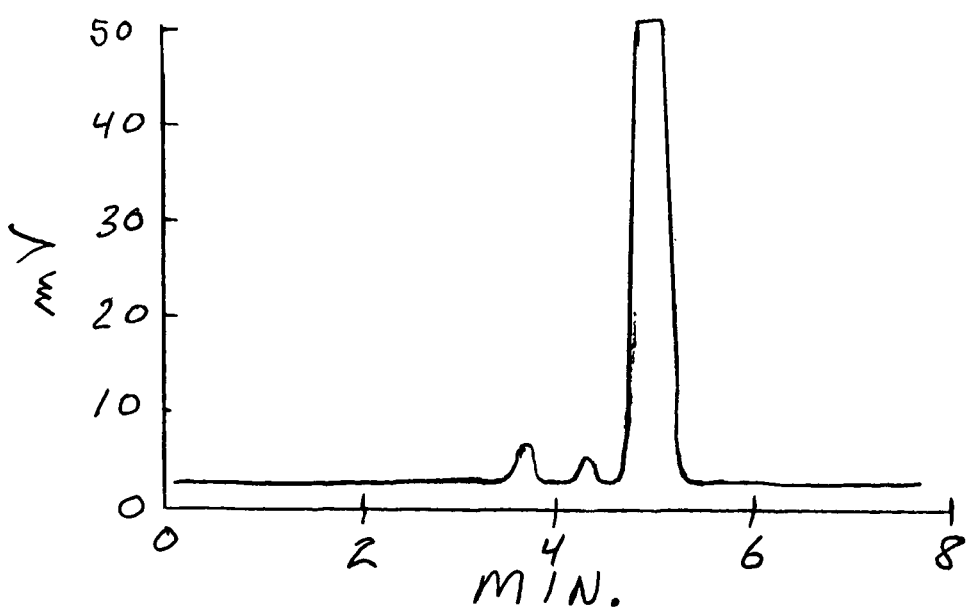
FIG. 2 is a reproduction of a chromatogram showing the separation of mPEG alcohol, mesylate activated mPEG and mesylate activated diol.

0.1 gram of mesylate activated 5,000 weight average molecular weight mPEG is mixed with 3 milliliters of water to produce a sample for injection. 5 microliters of the sample for injection is injected into a mobile phase of 52% A and 48% B (where A is 47% acetonitrile in water and B is 43% acetonitrile in water) at a mobile phase flow rate of 0.75 milliliters per minute and flowed through a 5 micrometer packing diameter Supelco LC-18 reverse phase column at a column temperature of 30 degrees Celsius, the column having an internal diameter of 4.6 millimeters and a length of 250 millimeters, followed by an evaporative light scattering detector to produce the chromatogram shown in FIG. 2. The chromatogram of FIG. 2 shows a peak at about 3.8 minutes for mPEG, a peak at about 4.4 minutes for the activated diol and a peak at about 4.9 minutes for the activated mPEG. The mole percent concentration of mPEG is determined by dividing the peak area of the mPEG peak by the combined peak areas of the mPEG, the activated mPEG and the activated diol peak areas and then multiplying by 100. The mole percent concentration of activated mPEG is determined by dividing the peak area of the activated mPEG peak by the combined peak areas of the mPEG, the activated mPEG and the activated diol peak areas and then multiplying by 100. The mole percent concentration of activated diol is determined by dividing the peak area of the activated diol peak by the combined peak areas of the mPEG, the activated mPEG and the activated diol peak areas and then multiplying by 100.

EXAMPLE 3

Figure 3:
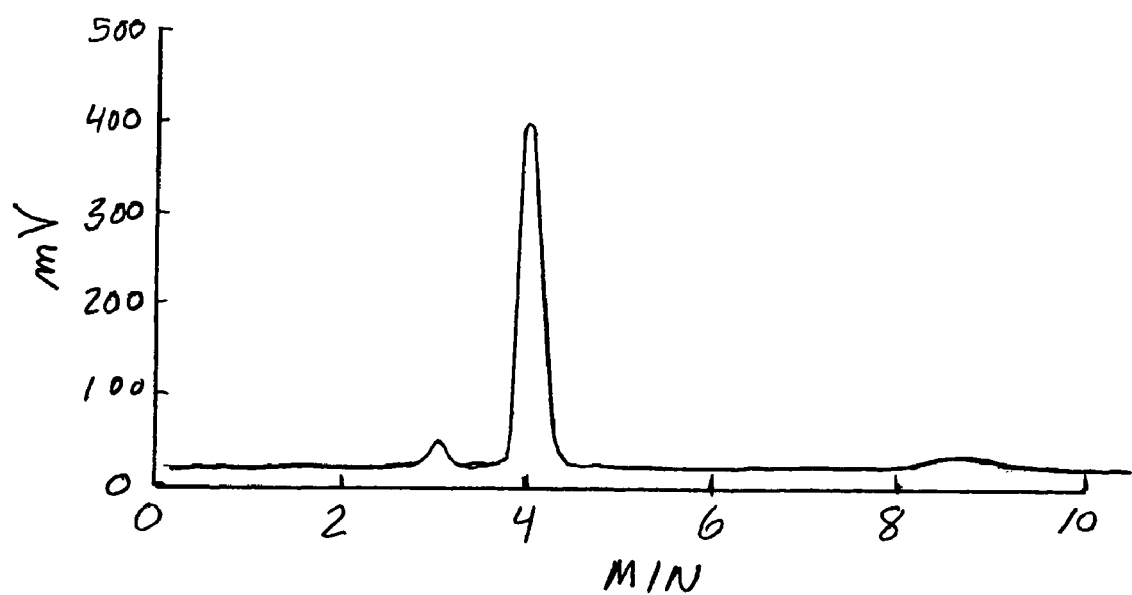
FIG. 3 is a reproduction of a chromatogram showing the separation of mPEG alcohol, para-nitrophenyl carbonate activated mPEG and para-nitrophenyl carbonate activated diol.

0.1 gram of para-nitro phenyl carbonate activated 20,000 weight average molecular weight mPEG is mixed with 3 milliliters of water to produce a sample for injection. 5 microliters of the sample for injection is injected into a mobile phase of 52% A and 48% B (where A is 47% acetonitrile in water and B is 43% acetonitrile in water) at a mobile phase flow rate of 0.75 milliliters per minute and flowed through a 5 micrometer packing diameter Jupiter C-18 reverse phase column at a column temperature of 29 degrees Celsius, the column having an internal diameter of 4.6 millimeters and a length of 150 millimeters, followed by an evaporative light scattering detector to produce the chromatogram shown in FIG. 3. The chromatogram of FIG. 3 shows a peak at about 3 minutes for mPEG, a peak at about 4.8 minutes for the activated mPEG and a small peak at about 8.5 minutes for activated diol. The mole percent concentration of mPEG is determined by dividing the peak area of the mPEG peak by the combined peak areas of the mPEG, the activated mPEG and the activated diol peak areas and then multiplying by 100. The mole percent concentration of activated mPEG is determined by dividing the peak area of the activated mPEG peak by the combined peak areas of the mPEG, the activated mPEG and the activated diol peak areas and then multiplying by 100. The mole percent concentration of activated diol is determined by dividing the peak area of the activated diol peak by the combined peak areas of the mPEG, the activated mPEG and the activated diol peak areas and then multiplying by 100.

Derivatized Activated mPEG

In another embodiment, the instant invention is a chemical analysis method for the determination of the above discussed $RO(CH_2CH_2O)_nH$, $RO(C_2H_4O)_nA$, and $AO(C_2H_4O)_nA$ in a mixture thereof, comprising the steps of: (a) derivatizing the A groups of the mixture with a derivatizing agent to form a derivatized mixture comprising $RO(CH_2CH_2O)_nH$, $RO(C_2H_4O)_nAD$, and $DAO(C_2H_4O)_nAD$, wherein AD is the derivatized A group; and (b) chromatographing a sample of the derivatized mixture by liquid chromatography under critical conditions to determine the relative amounts of $RO(CH_2CH_2O)_nH$, $RO(C_2H_4O)_nAD$, and $DAO(C_2H_4O)_nAD$ in the derivatized mixture. This embodiment of the instant invention is especially applicable when the activating group is hydrophilic, such as a group comprising, without limitation thereto, an aldehyde, a maleimide, an amine or a thiol. mPEGs activated with a hydrophilic group can be difficult to separate from mPEG alcohol, because the hydroxyl group of the mPEG alcohol is also hydrophilic. However, it has been discovered that if such activated mPEG is derivatized with a derivatizing agent which attaches a hydrophobic group to the A group of the activated mPEG, then the derivatized activated mPEG can be more readily separated from the non-activated PEG alcohol. Similarly, mPEGs activated with a hydrophilic group can be difficult to separate from PEG diols activated with two hydrophilic groups, because the methyl group of the mPEG alcohol is not very hydrophobic. However, it has been discovered that if the A groups of the activated mPEG and the di-activated PEG are derivatized with a derivatizing agent which attaches a hydrophobic group to the A groups on both the activated mPEG and the di-activated PEG, then the derivatized activated mPEG can be more readily separated from the derivatized di-activated PEG.

Examples of suitable derivatizing agents include aromatic/aliphatic aldehydes/ketones for reductive amination of mPEG/PEG activated with amine; aromatic/aliphatic disulfides to convert mPEG/PEG thiols to mixed disulfides; and aromatic/aliphatic hydrazines such as 1-(hydrazinocarbonylmethyl)pyridinium chloride or dinitro phenyl hydrazine) to convert mPEG/PEG activated with carbonyl groups to the corresponding hydrazone group.

The derivatizing agent most preferably imparts a detectable characteristic, e.g. ultra-violet (UV) chromaphore or fluorescent group, to the derivatized activated mPEG/PEG to allow the derivatized activated mPEG/PEG to be detected when it is eluted from the critical LC system. And, it should be understood that even when the activating group(s) A has (have) sufficient hydrophobic character to permit sufficient resolution of activated mPEG from di-activated PEG in the critical LC chromatogram, it may never-the-less be desirable to derivatize the activated mPEG and di-activated PEG using a derivatizing agent that imparts sufficient detectable characteristic to be detected when it is eluted from the critical LC system.

CONCLUSION

In conclusion, it should be readily apparent that although the invention has been described above in relation with its preferred embodiments, it should be understood that the instant invention is not limited thereby but is intended to cover all alternatives, modifications and equivalents that are included within the scope of the invention as defined by the following claims.

What is claimed is:

1. A chemical analysis method for the determination of $RO(CH_2CH_2O)_nH$, $RO(C_2H_4O)_nA$ having a molecular weight greater than 5,000 grams per mole, and $AO(C_2H_4O)_nA$ in a mixture thereof, wherein R is an alkyl group, A is a functional group for coupling with a surface or a biologically active material or other thing of use and n is an integer greater than 100, comprising the step of: chromatographing a sample of the mixture by reverse phase liquid chromatography under critical conditions to determine the relative amounts of $RO(CH_2CH_2O)_nH$, $RO(C_2H_4O)_nA$, and $AO(C_2H_4O)_nA$ in the mixture.

2. The method of claim 1, wherein R consists essentially of a methyl group.

3. The method of claim 1 wherein A comprises an aldehyde group.

4. The method of claim 3, wherein the aldehyde is propionaldehyde.

5. The method of claim 1 wherein A is propionaldehyde diacetal.

6. The method of claim 1 wherein A is mesylate.

7. The method of claim 1 wherein A is para-nitrophenyl carbonate.

8. The method of claim 1 wherein A comprises a maleimide group.

9. The method of claim 1 wherein A comprises an amine group.

10. The method of claim 1 wherein A comprises a thiol group.

11. The method of claim 1 wherein A comprises a dithiol group.

12. The method of claim 1 wherein the weight average molecular weight of the $RO(C_2H_4O)_nA$ is greater than 10,000 grams per mole.

* * * * *